(12) United States Patent
Mitani et al.

(10) Patent No.: US 8,477,235 B2
(45) Date of Patent: Jul. 2, 2013

(54) IMAGE PROCESSING DEVICE, IMAGE PROCESSING METHOD, PROGRAM, AND ELECTRONIC DEVICE

(75) Inventors: Satoshi Mitani, Kanagawa (JP); Nobuhiro Saijo, Tokyo (JP)

(73) Assignee: Sony Corporation, Tokyo (JP)

( * ) Notice: Subject to any disclaimer, the term of this patent is extended or adjusted under 35 U.S.C. 154(b) by 158 days.

(21) Appl. No.: 13/017,577

(22) Filed: Jan. 31, 2011

(65) Prior Publication Data

US 2011/0187899 A1 Aug. 4, 2011

(30) Foreign Application Priority Data

Feb. 4, 2010 (JP) ................................. 2010-022814

(51) Int. Cl.
*H04N 5/222* (2006.01)

(52) U.S. Cl.
USPC ............... 348/370; 348/68; 348/77; 348/371; 382/115; 382/116; 382/118; 382/254; 382/167; 250/339.01

(58) Field of Classification Search
USPC ........................................................ 348/370
See application file for complete search history.

(56) References Cited

U.S. PATENT DOCUMENTS

| | | | |
|---|---|---|---|
| 6,486,915 B2* | 11/2002 | Bell et al. ...................... | 348/362 |
| 2002/0051578 A1* | 5/2002 | Imagawa et al. ............... | 382/224 |
| 2003/0144584 A1* | 7/2003 | Mendelson .................... | 600/323 |
| 2006/0056661 A1* | 3/2006 | Einighammer et al. ....... | 382/115 |
| 2007/0106160 A1* | 5/2007 | Kilgore et al. ................. | 600/473 |
| 2008/0170846 A1* | 7/2008 | Wang ............................. | 396/182 |
| 2008/0177185 A1* | 7/2008 | Nakao et al. .................. | 600/476 |
| 2010/0271507 A1* | 10/2010 | Hung et al. .................... | 348/231.99 |

OTHER PUBLICATIONS

Yasuhiro Suzuki et al, Trans. Inst. Elect.Engnr.Jpn. Detection Method of Skin Region by Near-IR Spectrum Multi-Band, vol. 127 No. 4, pp. 583-590, 2007.

* cited by examiner

*Primary Examiner* — Roberto Velez
*Assistant Examiner* — Quan Pham
(74) *Attorney, Agent, or Firm* — K&L Gates LLP

(57) ABSTRACT

An image processing device for detecting a skin region representing a skin of a subject from a pickup image obtained by imaging said subject, the image processing device includes: a first irradiating section; a second irradiating section; an image pickup section; an adjusting section; and a skin detecting section.

13 Claims, 8 Drawing Sheets

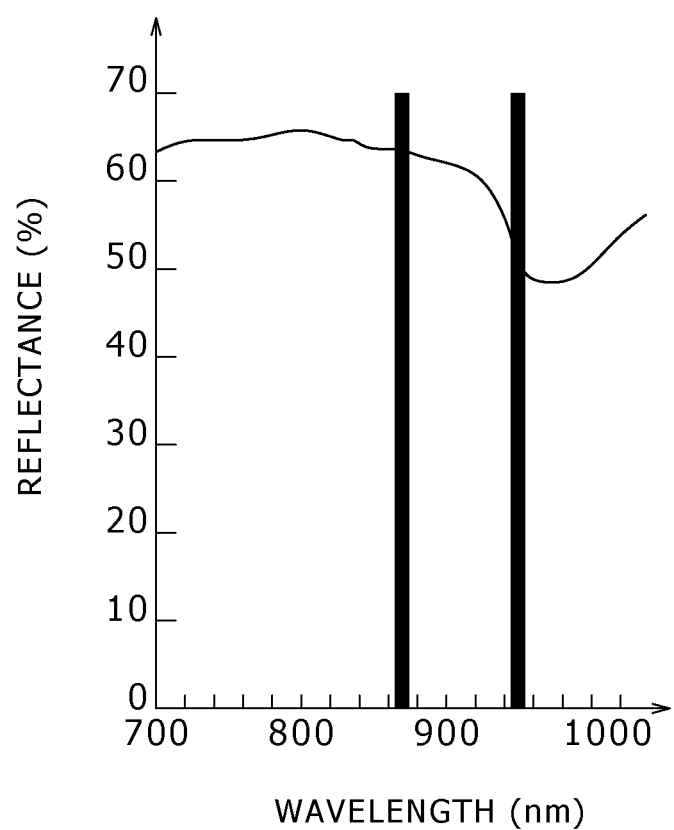
F I G . 2

HISTOGRAM OF OUTSIDE LIGHT IMAGE
AND LUMINANCE AVERAGE VALUE

HISTOGRAM OF OUTSIDE LIGHT IMAGE
AND PEAK VALUE

HISTOGRAM OF OUTSIDE LIGHT IMAGE AND
VALUE OF PIXEL INTEGRATION COUNT OF 80%

IMAGE PROCESSING DEVICE, IMAGE PROCESSING METHOD, PROGRAM, AND ELECTRONIC DEVICE

CROSS REFERENCES TO RELATED APPLICATIONS

The present application claims priority to Japanese Priority Patent Application JP 2010-022814 filed in the Japan Patent Office on Feb. 4, 2010, the entire content of which is hereby incorporated by reference.

BACKGROUND

The present application relates to an image processing device, an image processing method, a program, and an electronic device, and particularly to an image processing device, an image processing method, a program, and an electronic device that are suitable for use in extracting a skin region from a pickup image obtained by imaging a user, for example.

There is a skin recognition system that detects (recognizes) a skin region representing the skin of a human from a pickup image obtained by imaging a subject (see Yasuhiro Suzuki et al., IEEJ Transactions on Electronics, Information and Systems (proposition of a near-infrared multi-band skin detection method), Japan, 2007, Vol. 127, No. 4, for example).

In this skin recognition system, an LED (light emitting diode) for irradiating the subject with light of a wavelength $\lambda 1$ (for example a near-infrared ray of 870 [nm]) and an LED for irradiating the subject with light of a wavelength $\lambda 2$ (for example a near-infrared ray of 950 [nm]) different from the wavelength $\lambda 1$ are made to emit light alternately.

Incidentally, the combination of the wavelengths $\lambda 1$ and $\lambda 2$ is for example a combination such that the reflectance when the skin of a human is irradiated with light of the wavelength $\lambda 1$ is higher than the reflectance when the skin of the human is irradiated with light of the wavelength $\lambda 2$ and such that the reflectance when a thing other than the skin of a human is irradiated with light of the wavelength $\lambda 1$ is substantially the same as the reflectance when the thing is irradiated with light of the wavelength $\lambda 2$.

In the skin recognition system, a first pickup image is picked up when the LED for applying light of the wavelength $\lambda 1$ irradiates the subject with light of the wavelength $\lambda 1$.

In addition, a second pickup image is picked up when the LED for applying light of the wavelength $\lambda 2$ irradiates the subject with light of the wavelength $\lambda 2$.

Then, on the basis of the first pickup image and the second pickup image, a skin region is detected from one of the first pickup image and the second pickup image.

That is, as described above, a combination such that the reflectance when the skin of a human is irradiated with light of the wavelength $\lambda 1$ is higher than the reflectance when the skin of the human is irradiated with light of the wavelength $\lambda 2$ is adopted as combination of the wavelengths $\lambda 1$ and $\lambda 2$.

Thus, the luminance values of pixels forming the skin region in the first pickup image are relatively high values, and the luminance values of pixels forming the skin region in the second pickup image are relatively low values. Therefore difference values between the luminance values of the pixels forming the skin region in the first pickup image and the second pickup image are relatively high values.

In addition, as described above, a combination such that the reflectance when a thing other than the skin of a human is irradiated with light of the wavelength $\lambda 1$ is substantially the same as the reflectance when the thing other than the skin of a human is irradiated with light of the wavelength $\lambda 2$ is adopted as combination of the wavelengths $\lambda 1$ and $\lambda 2$.

Thus, the luminance values of pixels forming a region other than the skin region in the first pickup image are substantially the same as the luminance values of pixels forming the region other than the skin region in the second pickup image. Therefore difference values between the luminance values of the pixels forming the region other than the skin region in the first pickup image and the second pickup image are relatively low values.

Hence, in the skin recognition system, for example, a region corresponding to relatively high difference values can be detected as skin region.

SUMMARY

In the above-described skin recognition system, the difference values in the skin region in the first pickup image and the second pickup image can be substantially the same values as the difference values in the non-skin region (region other than the skin region) due to noise occurring in the first pickup image and the second pickup image, variation in amount of irradiation light of each LED, and the like.

In this case, accuracy of detection of the skin region is greatly decreased because the skin recognition system detects (determines) whether a region corresponding to difference values is a skin region or a non-skin region according to the magnitude of the difference values.

Accordingly, in order to prevent the accuracy of detection of the skin region from being decreased, the difference values in the skin region need to be sufficiently higher than the difference values in the non-skin region.

However, depending on a distance from the skin recognition system to the subject, the difference values in the skin region cannot be made sufficiently higher than the difference values in the non-skin region in some cases, and a detectable range in which the skin region can be detected with high accuracy may be limited.

Accordingly, it is conceivable that the detectable range may be extended by increasing the gain of a camera for picking up images of the subject so that the difference values in the skin region in the first pickup image and the second pickup image are sufficiently higher than the difference values in the non-skin region.

In addition, when the amount of irradiation light of each LED is less than an amount of irradiation light with which the skin region can be detected with high accuracy, it is conceivable that the gain of the camera may be increased to compensate for a shortage of the amount of irradiation light of each LED, and that the skin region of the subject may then be detected.

However, when the gain is increased ignoring outside light such as sunlight and light produced by lighting (an incandescent light or a fluorescent light) and the like, saturation caused by a camera (overexposure or the like) occurs, so that the skin region cannot be detected with high accuracy.

The present application has been made in view of such situations. It is desirable to adjust the gain of a camera and the like according to outside light such as sunlight and light produced by lighting and the like, and detect a skin region with high accuracy.

According to an embodiment, there is provided an image processing device for detecting a skin region representing a skin of a subject from a pickup image obtained by imaging the subject, the image processing device including: first irradiating means for irradiating the subject with light of a first wavelength; second irradiating means for irradiating the subject with light of a second wavelength different from the first wavelength; image pickup means for imaging the subject; adjusting means for adjusting a parameter of the image pickup means within a range in which a skin detectable condition for detecting the skin region is satisfied on a basis of an outside light image obtained by imaging the subject by the image pickup means in a state of the subject not being irradiated with light of the first wavelength or light of the second wavelength; and skin detecting means for detecting the skin region on a basis of a first pickup image obtained by imaging the subject when the subject is irradiated with light of the first wavelength by the image pickup means having the parameter adjusted by the adjusting means and a second pickup image obtained by imaging the subject when the subject is irradiated with light of the second wavelength by the image pickup means having the parameter adjusted by the adjusting means.

The adjusting means can adjust the parameter of the image pickup means within a range in which the skin detectable condition that a luminance value of a pixel forming the outside light image be equal to or lower than half of a maximum luminance value that can be obtained by imaging of the image pickup means is satisfied.

The adjusting means can adjust the parameter of the image pickup means within a range in which the skin detectable condition that the luminance value of the pixel forming the outside light image be half of the maximum luminance value that can be obtained by imaging of the image pickup means is satisfied.

The adjusting means can adjust the parameter of the image pickup means on a basis of an average value of luminance values of pixels forming the outside light image.

The adjusting means can adjust the parameter of the image pickup means on a basis of a luminance value of a maximum number of pixels among luminance values of pixels forming the outside light image.

The adjusting means can adjust the parameter of the image pickup means on a basis of a luminance value of a pixel when a luminance integration count obtained by performing integration starting with a pixel having a low luminance value becomes a predetermined value among luminance values of pixels forming the outside light image.

The adjusting means can adjust at least one of a gain of the image pickup means, receiving sensitivity, and light reception time as the parameter of the image pickup means.

The first irradiating means and the second irradiating means can apply infrared rays of respective different wavelengths.

One of the first irradiating means and the second irradiating means can apply light of a wavelength equal to or more than 930 [nm], and the other can apply light of less than 930 [nm].

According to an embodiment, there is provided an image processing method of an image processing device for detecting a skin region representing a skin of a subject from a pickup image obtained by imaging the subject, the image processing device including first irradiating means, second irradiating means, image pickup means, adjusting means, and skin detecting means, the image processing method including the steps of: the first irradiating means irradiating the subject with light of a first wavelength; the second irradiating means irradiating the subject with light of a second wavelength different from the first wavelength; the image pickup means imaging the subject; the adjusting means adjusting a parameter of the image pickup means within a range in which a skin detectable condition for detecting the skin region is satisfied on a basis of an outside light image obtained by imaging the subject by the image pickup means in a state of the subject not being irradiated with light of the first wavelength or light of the second wavelength; and the skin detecting means detecting the skin region on a basis of a first pickup image obtained by imaging the subject when the subject is irradiated with light of the first wavelength by the image pickup means having the parameter adjusted by the adjusting means and a second pickup image obtained by imaging the subject when the subject is irradiated with light of the second wavelength by the image pickup means having the parameter adjusted by the adjusting means.

According to an embodiment, there is provided a program for making a computer function as: adjusting means for adjusting a parameter of image pickup means within a range in which a skin detectable condition for detecting a skin region representing a skin of a subject is satisfied on a basis of an outside light image obtained by imaging the subject by the image pickup means in a state of the subject not being irradiated with light of a first wavelength or light of a second wavelength different from the first wavelength; and skin detecting means for detecting the skin region on a basis of a first pickup image obtained by imaging the subject when the subject is irradiated with light of the first wavelength by the image pickup means having the parameter adjusted by the adjusting means and a second pickup image obtained by imaging the subject when the subject is irradiated with light of the second wavelength by the image pickup means having the parameter adjusted by the adjusting means.

According to an embodiment, there is provided an electronic device including an image processing device for detecting a skin region representing a skin of a subject from a pickup image obtained by imaging the subject, wherein the image processing device includes: first irradiating means for irradiating the subject with light of a first wavelength; second irradiating means for irradiating the subject with light of a second wavelength different from the first wavelength; image pickup means for imaging the subject; adjusting means for adjusting a parameter of the image pickup means within a range in which a skin detectable condition for detecting the skin region is satisfied on a basis of an outside light image obtained by imaging the subject by the image pickup means in a state of the subject not being irradiated with light of the first wavelength or light of the second wavelength; and skin detecting means for detecting the skin region on a basis of a first pickup image obtained by imaging the subject when the subject is irradiated with light of the first wavelength by the image pickup means having the parameter adjusted by the adjusting means and a second pickup image obtained by imaging the subject when the subject is irradiated with light of the second wavelength by the image pickup means having the parameter adjusted by the adjusting means.

According to an embodiment, a parameter of image pickup means is adjusted within a range in which a skin detectable condition for detecting a skin region representing a skin of a subject is satisfied on a basis of an outside light image obtained by imaging the subject by the image pickup means in a state of the subject not being irradiated with light of a first wavelength or light of a second wavelength different from the first wavelength, and the skin region is detected on a basis of a first pickup image obtained by imaging the subject when the subject is irradiated with light of the first wavelength by the image pickup means having the parameter adjusted and a second pickup image obtained by imaging the subject when the subject is irradiated with light of the second wavelength by the image pickup means having the parameter adjusted.

According to the present application, a gain of a camera and the like are adjusted according to outside light such as sunlight and light produced by lighting and the like, and therefore a skin region can be detected with high accuracy.

Additional features and advantages are described herein, and will be apparent from the following Detailed Description and the figures.

BRIEF DESCRIPTION OF THE FIGURES

FIG. 2 is a diagram showing an example of a spectral reflection characteristic of the skin of a human;

DETAILED DESCRIPTION

Embodiments of the present application will be described below in detail with reference to the drawings.

The mode for carrying out the application (which mode will hereinafter be referred to as a present embodiment) will hereinafter be described. Incidentally, description will be made in the following order.

1. Present Embodiment (Example of Adjusting Gain of Camera on Basis of Average Luminance of Outside Light Image)
2. Examples of Modification
1. Present Embodiment
Example of Constitution of Information Processing System 1

Figure 1:
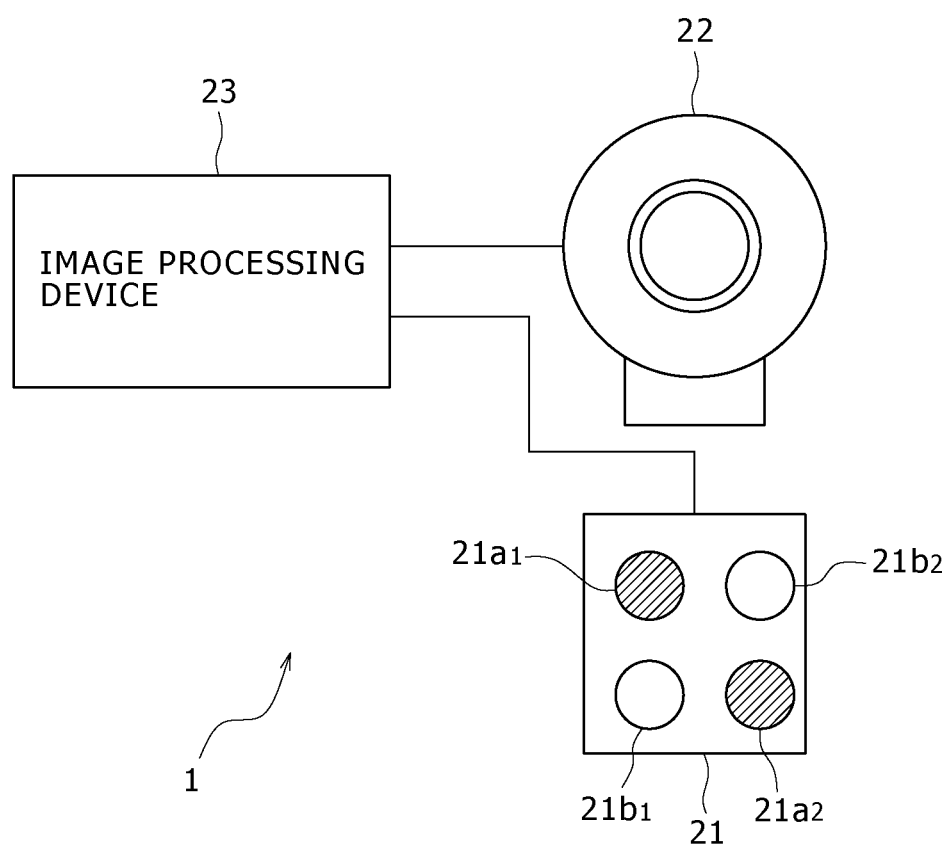
FIG. 1 is a block diagram showing an example of constitution of an information processing system to which the present application is applied.

FIG. 1 shows an example of constitution of an information processing system 1 according to the present embodiment.

The information processing system 1 performs a predetermined process according to a gesture (or a posture) using a hand of a user. The information processing system 1 includes a light emitting device 21, a camera 22, and an image processing device 23.

In order to make the information processing system 1 perform a predetermined process, the user changes the shape of a hand of the user in front of a lens of the camera 22.

At this time, the information processing system 1 recognizes the shape of the hand of the user, and performs the predetermined process in response to a result of the recognition.

Incidentally, suppose in the present embodiment that the user changes the shape of a hand in front of the lens of the camera 22, and that the user puts a hand of the user to a position closer to the lens of the camera 22 than a face, a chest or the like of the user and makes a gesture (posture).

The light emitting device 21 includes an LED 21$a$1 and an LED 21$a$2 for applying (emitting) light of a wavelength $\lambda 1$ (for example a near-infrared ray of 870 [nm]) and an LED 21$b$1 and an LED 21$b$2 for applying light of a wavelength $\lambda 2$ (for example a near-infrared ray of 950 [nm]) different from the wavelength $\lambda 1$.

Incidentally, in the following description, the LED 21$a$1 and the LED 21$a$2 will be referred to simply as an LED 21$a$ when the LED 21$a$1 and the LED 21$a$2 do not need to be distinguished from each other, and the LED 21$b$1 and the LED 21$b$2 will be referred to simply as an LED 21$b$ when the LED 21$b$1 and the LED 21$b$2 do not need to be distinguished from each other.

The light emitting device 21 makes the LED 21$a$ and the LED 21$b$ emit light alternately, for example, according to control from the image processing device 23.

The LED 21$a$ and the LED 21$b$ emit light alternately, for example, such that corresponding pixels of pickup images obtained by image pickup of the camera 22 when a subject having a same reflectance at the wavelengths $\lambda 1$ and $\lambda 2$ (for example a mirror surface or the like with a reflectance of 100%) is irradiated with light of the wavelength $\lambda 1$ and irradiated with light of the wavelength $\lambda 2$ have a same luminance value.

A combination of the wavelength $\lambda 1$ of the LED 21$a$ and the wavelength $\lambda 2$ of the LED 21$b$ is for example a combination such that the reflectance when the skin of a human is irradiated with light of the wavelength $\lambda 1$ is higher than the reflectance when the skin of the human is irradiated with light of the wavelength $\lambda 2$ and such that the reflectance when a thing other than the skin of a human is irradiated with light of the wavelength $\lambda 1$ is substantially the same as the reflectance when the thing is irradiated with light of the wavelength $\lambda 2$. That is, this combination is determined on the basis of a spectral reflection characteristic of the skin of a human.

Next, FIG. 2 shows a spectral reflection characteristic of the skin of a human.

Incidentally, this spectral reflection characteristic is universal irrespective of differences in color between the skins of humans (racial differences), states (suntans), or the like.

In FIG. 2, an axis of abscissas indicates the wavelength of irradiation light with which the skin of a human is irradiated, and an axis of ordinates indicates the reflectance of the irradiation light with which the skin of the human is irradiated.

It is known that the reflectance of irradiation light with which the skin of a human is irradiated peaks around 800 [nm], sharply decreases from about 900 [nm], has a minimum value around 1000 [nm], and rises again.

Specifically, for example, as shown in FIG. 2, the reflectance of reflected light obtained by irradiating the skin of a human with light of 870 [nm] is 63%, and the reflectance of reflected light obtained by irradiating the skin of a human with light of 950 [nm] is 50%.

This is specific to the skin of a human. The reflectance of an object (for example hair, clothes or the like) other than the skin of a human often changes gently in a range of about 800 to 1000 [nm].

In the present embodiment, a combination in which the wavelength $\lambda 1$ is set at 870 [nm] and the wavelength $\lambda 2$ is set at 950 [nm], for example, is adopted as a combination of the wavelength $\lambda 1$ and the wavelength $\lambda 2$ in the above-described spectral reflection characteristic. This combination is such that a difference in reflectance corresponding to the skin of a human is relatively large and such that a difference in reflectance corresponding to a part other than the skin of a human is relatively small.

Returning to FIG. 1, the camera 22 receives reflected light of outside light with which a subject is irradiated and reflected light of light having the wavelength $\lambda 1$ with which light the subject is irradiated by the LED 21$a$. The camera 22 supplies a first pickup image obtained as a result of the light reception to the image processing device 23.

In addition, the camera 22 receives the reflected light of the outside light with which the subject is irradiated and reflected light of light having the wavelength λ2 with which light the subject is irradiated by the LED 21b. The camera 22 supplies a second pickup image obtained as a result of the light reception to the image processing device 23.

Further, the camera 22 receives the reflected light of the outside light with which the subject is irradiated, and supplies an outside light image obtained as a result of the light reception to the image processing device 23.

The image processing device 23 controls the light emitting device 21 and the camera 22. Specifically, the image processing device 23 performs an adjusting process of adjusting the gain of the camera 22 and amounts of irradiation light of the LED 21a and the LED 21b in the light emitting device 21 on the basis of the outside light image and the like from the camera 22. Incidentally, details of the adjusting process will be described later with reference to a flowchart of FIG. 6.

In addition, the image processing device 23 calculates difference values between the luminance values of corresponding pixels in the first and second pickup images supplied from the camera 22, and detects a skin region in the first pickup image (or the second pickup image) on the basis of the calculated difference values.

Then, the image processing device 23 recognizes the shape of a hand of a user or the like on the basis of the detected skin region, and performs a predetermined process in response to a result of the recognition.

Example of Constitution of Image Processing Device 23

Figure 3:
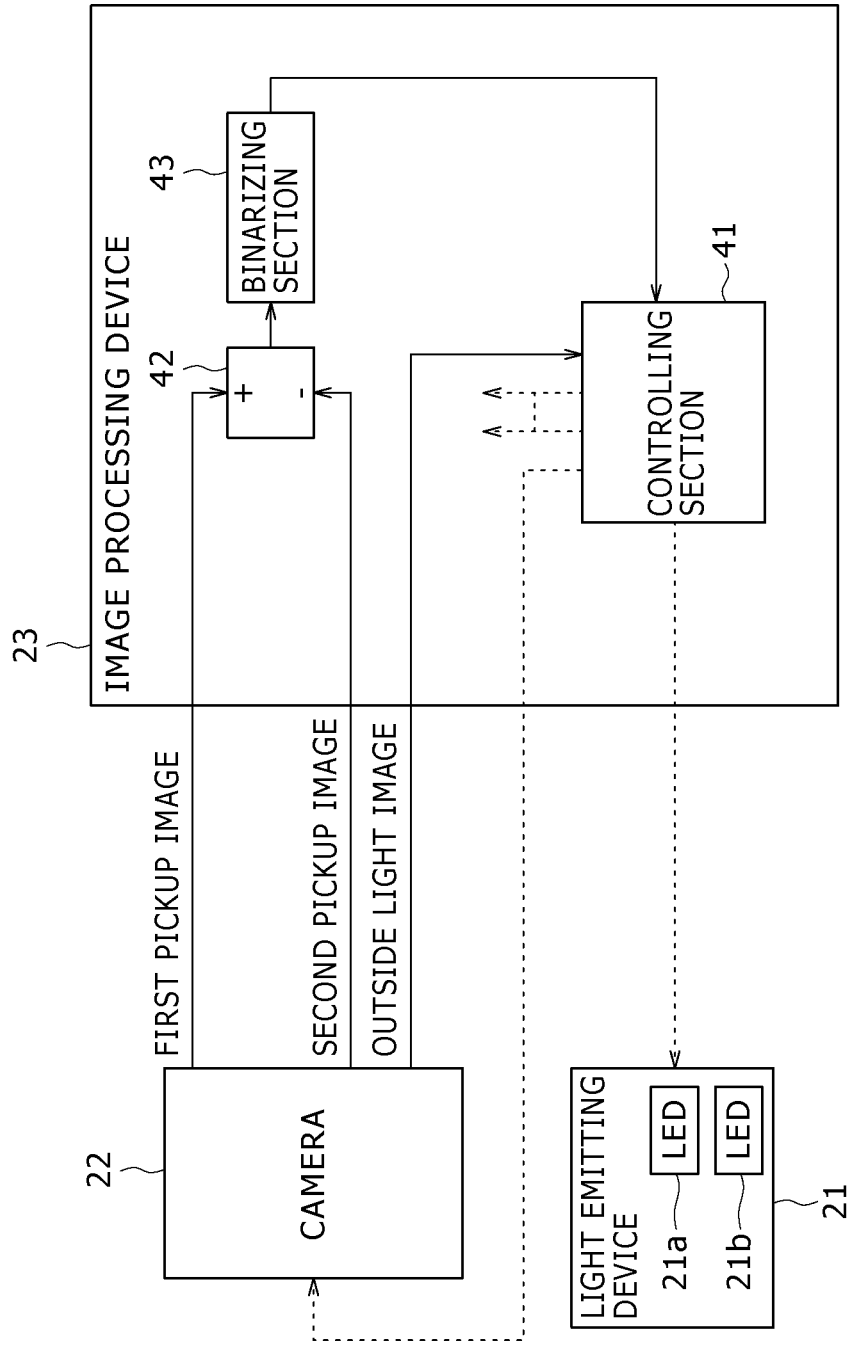
FIG. 3 is a block diagram showing an example of detailed constitution of an image processing device.

Next, FIG. 3 shows an example of constitution of the image processing device 23.

The image processing device 23 includes a controlling section 41, a calculating section 42, and a binarizing section 43.

The controlling section 41 controls the light emitting device 21 and the camera 22 to make the camera 22 pick up an image of a subject in a state of each of the LED 21a and the LED 21b being off, and make the camera 22 supply an outside light image obtained by the image pickup to the controlling section 41.

The controlling section 41 generates a histogram of luminance values of pixels forming the outside light image from the camera 22, and adjusts the gain of the camera 22 on the basis of the generated histogram.

Specifically, for example, on the basis of the generated histogram, the controlling section 41 adjusts the gain of the camera 22 within a range where a skin region can be detected with high accuracy even with noise occurring in the first and second pickup images, variations in the amounts of irradiation light of the LED 21a and the LED 21b, and the like without the camera 22 being saturated (overexposure or the like).

Figure 4:
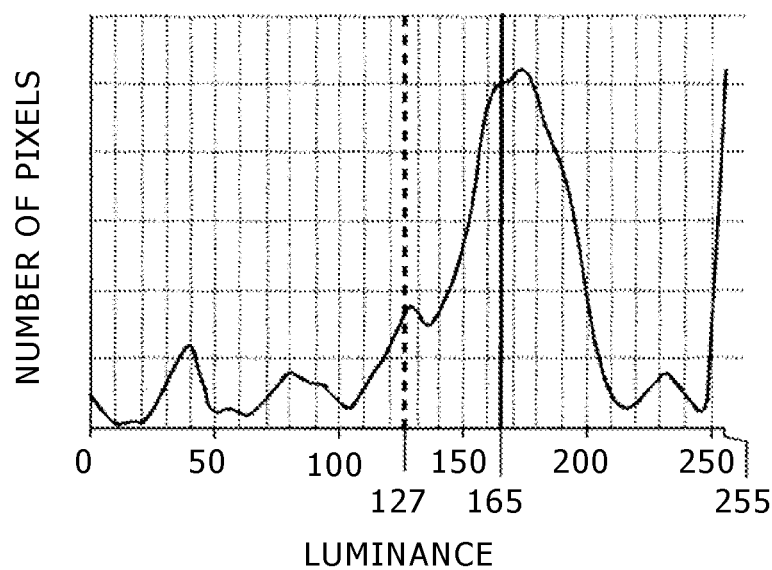
FIG. 4 is a diagram showing a first example of a histogram of luminance values of pixels forming an outside light image.

Next, FIG. 4 shows an example of a histogram generated by the controlling section 41.

In FIG. 4, an axis of abscissas indicates luminance values, and an axis of ordinates indicates total numbers of pixels having the luminance values on the axis of abscissas in an outside light image. Incidentally, suppose that the camera 22 generates images represented by 28 (=256) gradations by image pickup. The axis of abscissas therefore indicates values of 0 to 255 as luminance values.

The controlling section 41 generates a histogram as shown in FIG. 4 on the basis of the outside light image from the camera 22, and calculates a luminance average value indicating an average value of the luminance values of pixels forming the outside light image on the basis of the generated histogram.

Then, for example, on the basis of the calculated luminance average value, the controlling section 41 adjusts the gain of the camera 22 within a range where a skin region can be detected with high accuracy, or specifically within a range where the calculated luminance average value is equal to or less than half of a maximum luminance value that can be obtained by image pickup of the camera 22, for example.

Preferably, the controlling section 41 adjusts the gain of the camera 22 so that the calculated luminance average value becomes a luminance value half the maximum luminance value that can be assumed in the outside light image.

Specifically, as shown in FIG. 4, for example, when the controlling section 41 calculates a luminance average value of 165 (represented by a thick vertical line in FIG. 4), the controlling section 41 adjusts the gain so that the luminance average value of 165 becomes a luminance value of 127 (represented by a thick dotted line in FIG. 4), which is half the maximum luminance value of 255 that can be obtained by image pickup of the camera 22.

After adjusting the gain, the controlling section 41 controls the LED 21a and the LED 21b of the light emitting device 21 to make the LED 21a and the LED 21b emit light alternately. In addition, the controlling section 41 controls the camera 22 to make the camera 22 pick up an image of a subject and supply a first pickup image and a second pickup image obtained by the image pickup to the calculating section 42.

Further, the controlling section 41 controls the calculating section 42 and the binarizing section 43 to make the calculating section 42 and the binarizing section 43 detect a skin region on the basis of the first pickup image and the second pickup image.

When the controlling section 41 obtains a detection result indicating that a skin region can be detected as a skin region detection result from the binarizing section 43, the controlling section 41 adjusts the amounts of irradiation light of the LED 21a and the LED 21b to be minimum necessary amounts of irradiation light with which the skin region can be detected with high accuracy, by decreasing the amounts of irradiation light of the LED 21a and the LED 21b.

In addition, when the controlling section 41 obtains a detection result indicating that the skin region cannot be detected as a skin region detection result from the binarizing section 43 because the detection of the skin region has been rendered impossible by excessively decreasing the amounts of irradiation light of the LED 21a and the LED 21b, the controlling section 41 adjusts the gain of the camera 22 to be higher than the present gain so that the skin region can be detected.

After adjusting the gain of the camera 22 and the amounts of irradiation light of the LED 21a and the LED 21b, in order to perform a process based on the skin region detection result, the controlling section 41 controls the calculating section 42 and the binarizing section 43 to make the calculating section 42 and the binarizing section 43 detect the skin region on the basis of the first pickup image and the second pickup image.

The controlling section 41 then performs a process based on the skin region detection result from the binarizing section 43. Specifically, for example, the controlling section 41 recognizes a gesture or a posture of the user on the basis of the detection result from the binarizing section 43, and performs a process corresponding to the recognized gesture or the like.

The calculating section 42 smoothes the first pickup image and the second pickup image from the camera 22 using an LPF (low-pass filter). Then, the calculating section 42 calculates difference values between the first pickup image and the second pickup image after being smoothed, and supplies a difference image formed by pixels having the calculated difference values as pixel values to the binarizing section 43.

The binarizing section 43 binarizes the difference image from the calculating section 42, detects a skin region in the first pickup image (or the second pickup image) on the basis of a binarized skin image obtained as a result of the binarization, and supplies a result of the detection to the controlling section 41.

Figure 5:
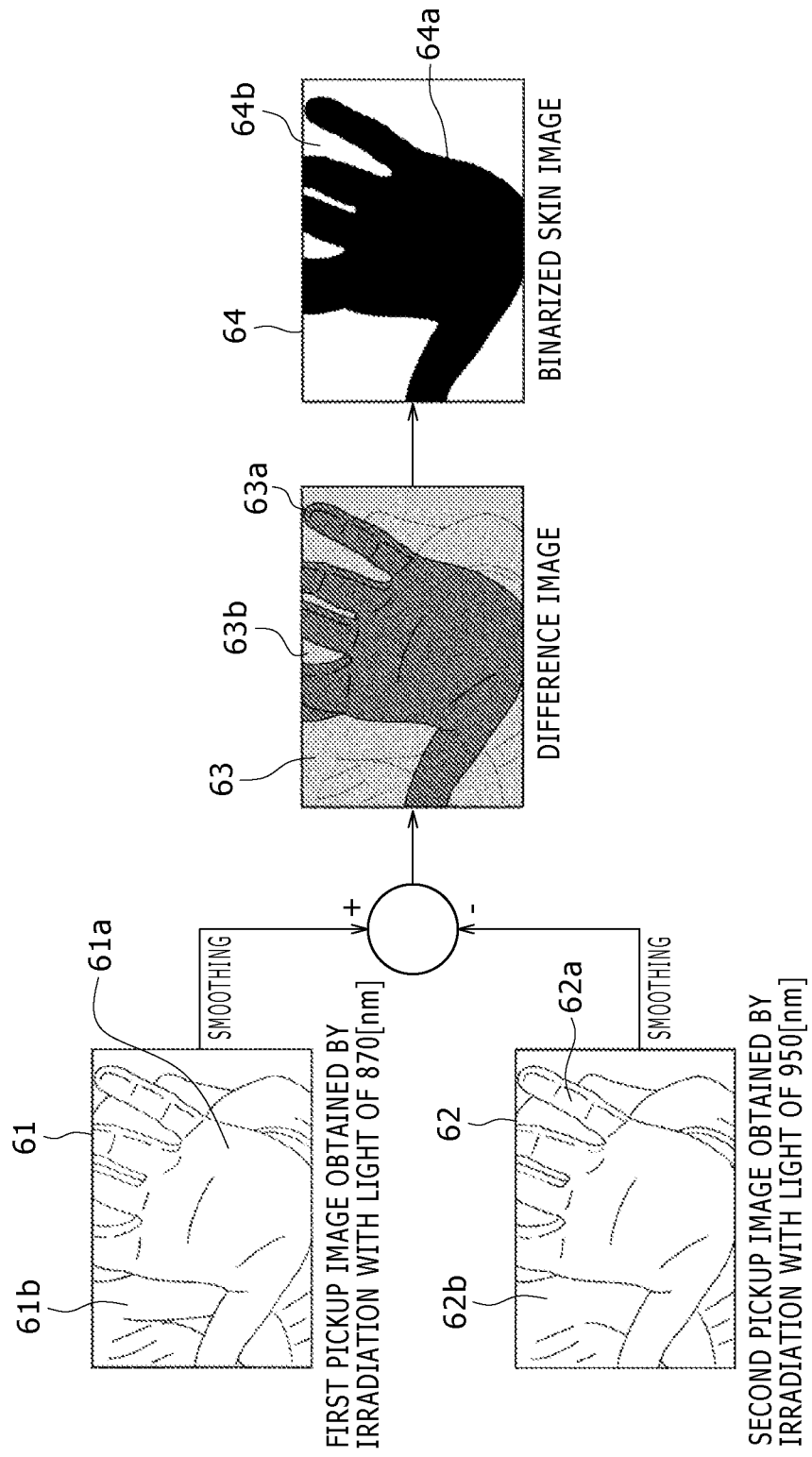
FIG. 5 is a diagram showing an example of processes performed by a calculating section and a binarizing section.

Next, FIG. 5 shows details of the processes performed by the calculating section 42 and the binarizing section 43.

The calculating section 42 is supplied from the camera 22 with a first pickup image 61 including a skin region 61a and a non-skin region 61b (region other than the skin region 61a) and a second pickup image 62 including a skin region 62a and a non-skin region 62b (region other than the skin region 62a).

The calculating section 42 smoothes the first pickup image 61 and the second pickup image 62 supplied from the camera 22 using an LPF. Then, the calculating section 42 calculates difference values between the luminance values of corresponding pixels of the first pickup image 61 after being smoothed and the second pickup image 62 after being smoothed, generates a difference image 63 having the difference values as pixel values, and supplies the difference image 63 to the binarizing section 43.

The binarizing section 43 subjects the difference image 63 from the calculating section 42 to binarization, which sets pixel values equal to or higher than a binarizing threshold value used for the binarization among the pixel values of the pixels forming the difference image 63 to one and which sets pixel values lower than the binarizing threshold value among the pixel values of the pixels forming the difference image 63 to zero.

Noise occurring in the first pickup image and the second pickup image, variations in the amounts of irradiation light of the LED 21a and the LED 21b, or the like needs to be prevented from causing the pixel values of pixels forming the skin region 63a in the difference image 63 and the pixel values of pixels forming the non-skin region 63b in the difference image 63 to be similar values, which renders accurate binarization impossible.

Thus, the gain of the camera 22, the amounts of irradiation light of the LED 21a and the LED 21b, or the like is adjusted so that the pixel values of the pixels forming the skin region 63a in the difference image 63 are equal to or higher than a skin detection enabling value (value sufficiently higher than the pixel values of the pixels forming the non-skin region 63b in the difference image 63) enabling the detection of the skin region with high accuracy, that is, so that the skin region can be detected with high accuracy.

Because the skin region 63a in the difference image 63 is formed by pixels having the difference values between the skin region 61a and the skin region 62a as pixel values, the pixel values of the pixels forming the skin region 63a are relatively high values.

Because the non-skin region 63b in the difference image 63 is formed by pixels having the difference values between the non-skin region 61b and the non-skin region 62b as pixel values, the pixel values of the pixels forming the non-skin region 63b are relatively low values.

Therefore the binarization performed by the binarizing section 43 converts the difference image 63 into a binarized skin image 64 including a skin region 64a in which the pixel values of the pixels forming the skin region 63a are converted to one and a non-skin region 64b in which the pixel values of the pixels forming the non-skin region 63b are converted to zero.

The binarizing section 43 then supplies the skin region 64a in the binarized skin image 64 obtained by the binarization to the controlling section 41 together with a detection result indicating that the skin of the subject can be detected.

Incidentally, when the skin region 64a is not present in the binarized skin image 64 obtained by the binarization, that is, when the skin of the subject cannot be detected, the binarizing section 43 supplies a detection result indicating that the skin of the subject cannot be detected to the controlling section 41.

Details of Adjusting Process Performed by Image Processing Device 23

Figure 6:
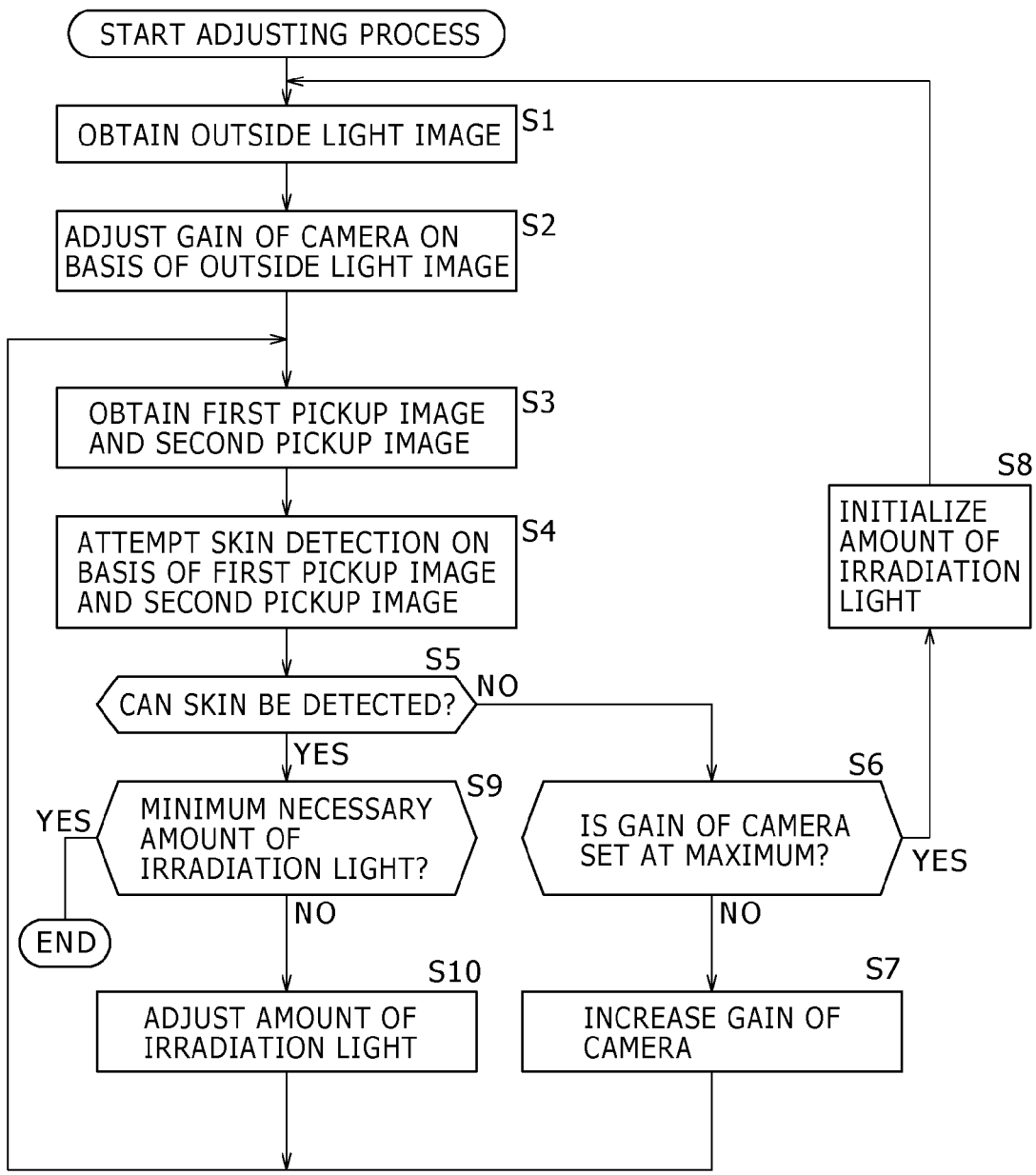
FIG. 6 is a flowchart of assistance in explaining an adjusting process performed by the image processing device.

The adjusting process performed by the image processing device 23 will next be described with reference to a flowchart of FIG. 6.

In step S1, the controlling section 41 controls the light emitting device 21 and the camera 22 to make the camera 22 pick up an image of a subject in a state of the LED 21a and the LED 21b of the light emitting device 21 being off, and obtains an outside light image obtained by the image pickup from the camera 22.

In step S2, for example, the controlling section 41 generates a histogram on the basis of the outside light image from the camera 22, and calculates a luminance average value of luminance values of pixels forming the outside light image on the basis of the generated histogram.

The controlling section 41 then adjusts the gain of the camera 22 on the basis of the calculated luminance average value so that the calculated luminance average value is equal to or lower than half the maximum luminance value that can be obtained by the image pickup of the camera 22.

Preferably, the controlling section 41 adjusts the gain of the camera 22 so that the calculated luminance average value is a luminance value half the maximum luminance value that can be obtained by the image pickup of the camera 22.

In step S3, the controlling section 41 controls the light emitting device 21 and the camera 22 to make the camera 22 pick up an image of the subject in a state of the LED 21a of the LED 21a and the LED 21b being on and supply a first pickup image obtained by the image pickup to the calculating section 42.

In addition, the controlling section 41 controls the light emitting device 21 and the camera 22 to make the camera 22 pick up an image of the subject in a state of the LED 21b of the LED 21a and the LED 21b being on and supply a second pickup image obtained by the image pickup to the calculating section 42.

The calculating section 42 thereby obtains the first pickup image and the second pickup image from the camera 22.

In step S4, the calculating section 42 and the binarizing section 43 attempt to detect a skin region in the first pickup image (or the second pickup image) on the basis of the first pickup image and the second pickup image obtained by the image pickup of the camera 22.

Specifically, for example, the calculating section 42 smoothes the first pickup image and the second pickup image from the camera 22 using an LPF. Then, the calculating section 42 calculates difference values between the first pickup image and the second pickup image after being smoothed, and supplies a difference image formed by pixels having the calculated difference values as pixel values to the binarizing section 43.

The binarizing section 43 binarizes the difference image from the calculating section 42, and attempts to detect a skin region in the first pickup image (second pickup image) on the basis of a binarized skin image obtained as a result of the binarization.

Then, the binarizing section 43 supplies a detection result indicating whether a skin region can be detected to the controlling section 41.

In step S5, the controlling section 41 determines whether a skin region can be detected on the basis of the detection result from the binarizing section 43. When the controlling section 41 determines that a skin region cannot be detected, the controlling section 41 advances the process to step S6.

In step S6, the controlling section 41 determines whether the gain adjusted in previous step S2 is a maximum gain to which adjustment can be made. When the controlling section 41 determines that the gain adjusted in previous step S2 is not the maximum gain, the controlling section 41 advances the process to step S7.

In step S7, the controlling section 41 controls the camera 22 to adjust the gain of the camera 22 to be higher than the gain set at present. The process then returns to step S3, where the calculating section 42 obtains a new first pickup image and a new second pickup image obtained by image pickup of the camera 22 after the gain is adjusted. A similar process is thereafter performed.

When the controlling section 41 determines in step S6 that the gain adjusted in previous step S2 is the maximum gain to which adjustment can be made, the gain cannot be adjusted to be higher. Therefore the controlling section 41 advances the process to step S8.

In step S8, the controlling section 41 controls the light emitting device 21 to initialize the amounts of irradiation light of the LED 21a and the LED 21b to a predetermined value, and returns the process to step S1 to repeat the adjusting process.

That is, when the process is advanced to step S8, it is considered that a skin region cannot be detected because the amounts of irradiation light of the LED 21a and the LED 21b have been decreased too much in step S10 to be described later. Thus, the amounts of irradiation light of the LED 21a and the LED 21b are initialized to a predetermined value, and the adjusting process is repeated.

When the controlling section 41 determines in step S5 that a skin region can be detected on the basis of the detection result from the binarizing section 43, on the other hand, the controlling section 41 advances the process to step S9. Incidentally, in this case, the binarizing section 43 has supplied the generated binarized skin image and the difference image from the calculating section 42 to the controlling section 41 together with the detection result indicating that a skin region can be detected.

In step S9, the controlling section 41 determines whether the amounts of irradiation light of the LED 21a and the LED 21b are a minimum amount of irradiation light necessary to detect a skin region on the basis of the binarized skin image and the difference image from the binarizing section 43.

Specifically, for example, on the basis of the binarized skin image from the binarizing section 43, the controlling section 41 extracts a skin region corresponding to a skin region (region formed by pixels having a pixel value of one, for example) in the binarized skin image from the difference image from the binarizing section 43.

Then, the controlling section 41 determines that the amounts of irradiation light of the LED 21a and the LED 21b are the minimum necessary amount of irradiation light when the pixel values of pixels forming the extracted skin region in the difference image are substantially equal to a skin detection enabling value (a value sufficiently higher than the pixel values of pixels forming a non-skin region in the difference image from the calculating section 42). When the pixel values of the pixels forming the extracted skin region in the difference image are higher than the skin detection enabling value, the controlling section 41 determines that the amounts of irradiation light of the LED 21a and the LED 21b are not the minimum necessary amount of irradiation light.

Specifically, for example, the controlling section 41 determines that the amounts of irradiation light of the LED 21a and the LED 21b are the minimum necessary amount of irradiation light when an average value of the pixel values of the pixels forming the extracted skin region in the difference image is substantially equal to the skin detection enabling value. The controlling section 41 determines that the amounts of irradiation light of the LED 21a and the LED 21b are not the minimum necessary amount of irradiation light when the average value of the pixel values of the pixels forming the extracted skin region in the difference image is higher than the skin detection enabling value.

When the controlling section 41 determines in step S9 that the amounts of irradiation light of the LED 21a and the LED 21b are not the minimum amount of irradiation light necessary to detect the skin region, the controlling section 41 advances the process to step S10.

In step S10, the controlling section 41 controls the light emitting device 21 to adjust the amounts of irradiation light of the LED 21a and the LED 21b to be the minimum amount of irradiation light necessary to detect the skin region by decreasing the amounts of irradiation light of the LED 21a and the LED 21b.

That is, for example, the controlling section 41 adjusts the amounts of irradiation light of the LED 21a and the LED 21b so that the luminance values of pixels forming the skin region in the first pickup image and the second pickup image obtained by image pickup of the camera 22 are minimum necessary luminance values enabling the skin region to be detected with high accuracy, that is, so that the average value of the pixel values of the pixels forming the skin region in the difference image is substantially equal to the skin detection enabling value.

After completing the process of step S10, the controlling section 41 returns the process to step S3. In step S3, the calculating section 42 obtains a first pickup image and a second pickup image obtained from the camera 22 in response to the turning on of the LED 21a and the LED 21b whose amounts of irradiation light have been adjusted. A similar process is thereafter performed.

Incidentally, the controlling section 41 ends the adjusting process when the controlling section 41 determines in step S9 that the amounts of irradiation light of the LED 21a and the LED 21b are the minimum amount of irradiation light necessary to detect the skin region.

As described above, in the adjusting process, for example, the controlling section 41 adjusts the gain of the camera 22 so that a luminance average value of luminance values of pixels forming an outside light image is a luminance value half the maximum luminance value that can be obtained by the image pickup of the camera 22.

In this case, the controlling section 41 adjusts the gain of the camera 22 to a maximum within a range where the skin region can be detected with high accuracy, or specifically within a range where the calculated luminance average value is equal to or lower than half of the maximum luminance value that can be obtained by the image pickup of the camera 22, for example. It is therefore possible to extend a detectable range in which the skin region can be detected while maintaining accuracy of detection of the skin region.

In addition, in the adjusting process, the amounts of irradiation light of the LED 21a and the LED 21b are decreased to the minimum amount of irradiation light necessary to detect the skin region. It is therefore possible to save power by reducing power necessary for the irradiation of the LED 21a and the LED 21b while maintaining the accuracy of detection of the skin region.

2. Examples of Modification

In the adjusting process of the present embodiment, the controlling section 41 generates the luminance average value of an outside light image on the basis of the histogram of the outside light image from the camera 22, and adjusts the gain of the camera 22 on the basis of the generated luminance average value. However, a method of adjusting the gain of the camera 22 is not limited to this.

Figure 7:
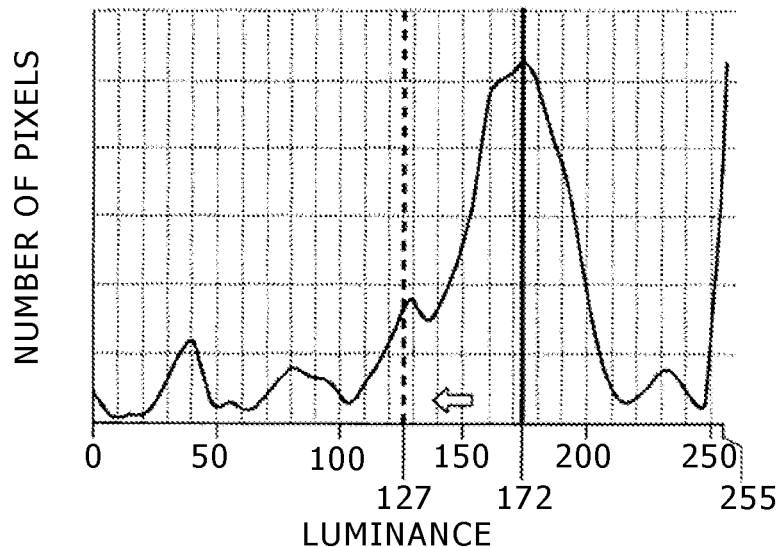
FIG. 7 is a diagram showing a second example of a histogram of luminance values of pixels forming an outside light image.

Specifically, for example, as shown in FIG. 7, the controlling section 41 may adjust the gain of the camera 22 so that a peak value (172 in this case) representing a luminance value when the number of pixels is a maximum in a histogram generated on the basis of an outside light image from the camera 22 becomes equal to or lower than half of the maximum luminance value that can be obtained by the image pickup of the camera 22.

Incidentally, when a luminance value of 255 is the peak value in the case shown in FIG. 7, the controlling section 41 may calculate a peak value after excluding a part where the luminance value is 255 (saturated), and adjust the gain of the camera 22 on the basis of the calculated peak value.

Figure 8:
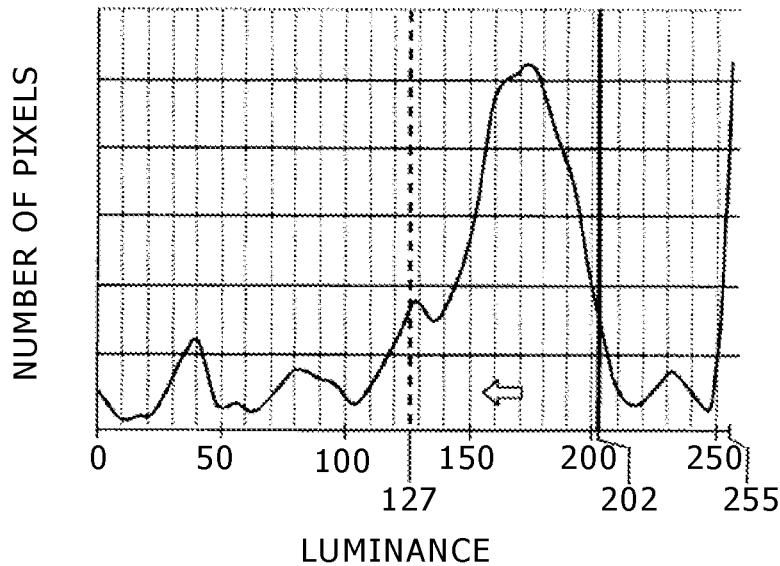
FIG. 8 is a diagram showing a third example of a histogram of luminance values of pixels forming an outside light image.

In addition, for example, as shown in FIG. 8, the controlling section 41 can adjust the gain of the camera 22 so that a luminance value determined on the basis of a pixel integration count indicating the number of pixels obtained by sequential integration (addition) starting with a pixel having a low luminance value becomes equal to or lower than half of the maximum luminance value that can be obtained by the image pickup of the camera 22 in a histogram generated on the basis of an outside light image from the camera 22.

Specifically, for example, the controlling section 41 can adjust the gain of the camera 22 so that the luminance value (202 in the present case) of a pixel integrated when the pixel integration count is the number of pixels corresponding to 80% of a total number of pixels in the histogram becomes equal to or lower than half of the maximum luminance value that can be obtained by the image pickup of the camera 22.

In the present embodiment, the controlling section 41 adjusts the gain of the camera 22 on the basis of the histogram of an outside light image. However, the controlling section 41 can be configured to adjust at least one of the gain of the camera 22, receiving sensitivity, exposure (light reception) time and the like.

In addition, in the present embodiment, the binarizing section 43 binarizes the difference image 63 from the calculating section 42 as it is. However, the difference image 63 can be binarized after pixel values of pixels forming the difference image 63 are each normalized (divided) by the luminance value of a corresponding pixel of pixels forming the first pickup image 61. Incidentally, the binarizing section 43 may binarize the difference image 63 after normalizing the difference image 63 using the second pickup image 62 in place of the first pickup image 61.

In the present embodiment, the first wavelength of light emitted by the LED 21a is set at 870 [nm], and the second wavelength of light emitted by the LED 21b is set at 950 [nm]. However, the combination of the wavelengths is not limited to this.

That is, the combination of the wavelengths may be any combination as long as a difference value between the reflectance at the first wavelength and the reflectance at the second wavelength is sufficiently high as compared with a difference value between reflectances obtained for things other than the skin of a user.

Specifically, as is clear from FIG. 2, for example, the LED 21a can be configured to apply irradiation light of the wavelength $\lambda 1$ less than 930 [nm], and the LED 21b can be configured to apply irradiation light of the wavelength $\lambda 2$ equal to or more than 930 [nm], as in not only the combination of 870 [nm] and 950 [nm] but also a combination of 800 [nm] and 950 [nm], a combination of 870 [nm] and 1000 [nm], a combination of 800 [nm] and 1000 [nm], or the like.

In addition, in the present embodiment, the light emitting device 21 makes the LED 21a and the LED 21b emit light separately from each other. However, the first pickup image and the second pickup image can be obtained by making the LED 21a and the LED 21b emit light simultaneously.

Specifically, for example, in place of the camera 22, two cameras having similar functions to those of the camera 22 are provided in proximity to each other. A filter passing only light of the first wavelength is provided to a front surface of one of the two cameras, and a filter passing only light of the second wavelength is provided to a front surface of the other camera.

In this case, even when the LED 21a and the LED 21b are made to emit light simultaneously, only the light of the first wavelength enters the one camera. Therefore the first pickup image can be obtained in the one camera. In addition, only the light of the second wavelength enters the other camera. Therefore the second pickup image can be obtained in the other camera.

In the present embodiment, description has been made supposing that the number of LEDs 21a and the number of LEDs 21b are each two. However, the numbers of such LEDs are not limited to this.

In the present embodiment, description has been made of the information processing system 1. The information processing system 1 can be incorporated into an electronic device such for example as a personal computer, and the personal computer can perform a process based on a gesture or the like corresponding to a skin region detected by the information processing system 1.

The series of processes described above can be carried out not only by dedicated hardware but also by software. When the series of processes is to be carried out by software, a program constituting the software is installed from a recording medium onto a so-called embedded computer or for example a general-purpose personal computer enabled to perform various functions by installing various programs onto the personal computer.

Example of Configuration of Computer

Figure 9:
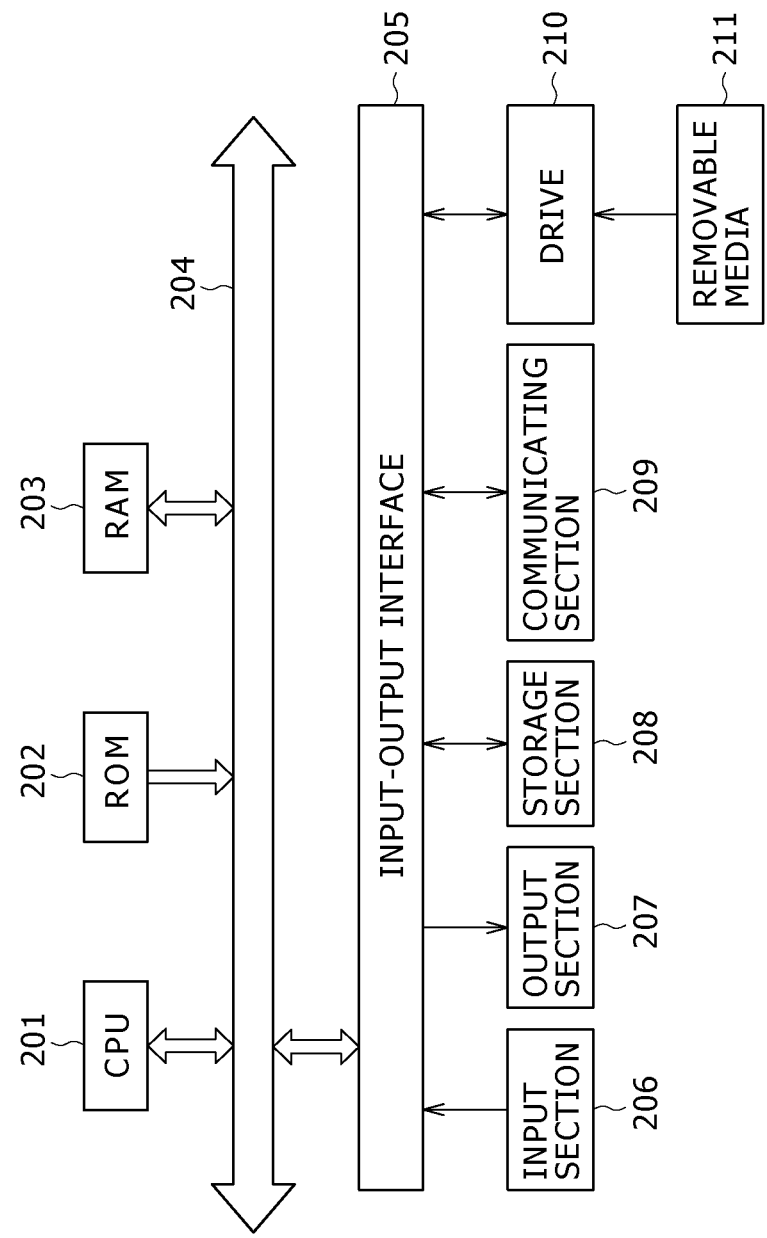
FIG. 9 is a block diagram showing an example of configuration of a computer.

Next, FIG. 9 shows an example of configuration of a personal computer that performs the series of processes described above by a program.

A CPU (Central Processing Unit) 201 performs various processes according to a program stored in a ROM (Read Only Memory) 202 or a storage section 208. A RAM (Random Access Memory) 203 stores the program being executed by the CPU 201, data, and the like as appropriate. The CPU 201, the ROM 202, and the RAM 203 are interconnected via a bus 204.

The CPU 201 is also connected with an input-output interface 205 via the bus 204. The input-output interface 205 is connected with an input section 206 including a keyboard, a mouse, a microphone and the like and an output section 207 including a display, a speaker, and the like. The CPU 201 performs various processes in response to a command input from the input section 206. The CPU 201 then outputs results of the processes to the output section 207.

The storage section 208 connected to the input-output interface 205 is formed by a hard disk, for example. The storage section 208 stores the program executed by the CPU 201 and various data. A communicating section 209 communicates with an external device via a network such as the Internet, a local area network, and the like.

In addition, the program may be obtained via the communicating section 209, and stored in the storage section 208.

When removable media 211 such as a magnetic disk, an optical disk, a magneto-optical disk, a semiconductor memory and the like are loaded into a drive 210 connected to the input-output interface 205, the drive 210 drives the removable media to obtain programs, data and the like stored on the removable media. The obtained programs and the obtained data are transferred to the storage section 208 and stored in the storage section 208 as demanded.

As shown in FIG. 9, for example, the recording medium on which the program installed on the computer and set in a state of being executable by the computer is recorded (stored) is formed by the removable media 211 as packaged media including a magnetic disk (including a flexible disk), an optical disk (including CD-ROM (Compact Disc-Read Only Memory) and DVD (Digital Versatile Disc)), a magneto-optical disk (including MD (Mini-Disc)), a semiconductor memory and the like, or formed by the ROM 202, the hard disk forming the storage section 208, or the like where the program is stored temporarily or permanently. The program is recorded onto the recording medium as required using a wire or wireless communication medium such as a local area network, the Internet, digital satellite broadcasting or the like via the communicating section 209 as an interface such as a router, a modem or the like.

It is to be noted that in the present specification, the steps describing the series of processes described above include not only processes carried out in time series in the described order but also processes carried out in parallel or individually and not necessarily in time series.

In addition, in the present specification, a system refers to an apparatus as a whole formed by a plurality of devices.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. An image processing device for detecting a skin region representing a skin of a subject from a pickup image obtained by imaging said subject, the image processing device comprising:
    first irradiating means for irradiating said subject with light of a first wavelength;
    second irradiating means for irradiating said subject with light of a second wavelength different from said first wavelength;
    image pickup means for imaging said subject;
    adjusting means for adjusting a parameter of said image pickup means within a range in which a skin detectable condition for detecting said skin region is satisfied on a basis of an outside light image obtained by imaging said subject by said image pickup means in a state of said subject not being irradiated with light of said first wavelength or light of said second wavelength; and
    skin detecting means for detecting said skin region on a basis of a first pickup image obtained by imaging said subject when said subject is irradiated with light of said first wavelength by said image pickup means having the parameter adjusted by said adjusting means and a second pickup image obtained by imaging said subject when said subject is irradiated with light of said second wavelength by said image pickup means having the parameter adjusted by said adjusting means
    wherein said adjusting means adjusts the parameter of said image pickup means within a range in which said skin detectable condition that a luminance value of a pixel forming said outside light image be equal to or lower than half of a maximum luminance value that can be obtained by imaging of said image pickup means is satisfied.

2. The image processing device according to claim 1, wherein said adjusting means adjusts the parameter of said image pickup means within a range in which said skin detectable condition that the luminance value of the pixel forming said outside light image be half of the maximum luminance value that can be obtained by imaging of said image pickup means is satisfied.

3. The image processing device according to claim 1, wherein said adjusting means adjusts the parameter of said image pickup means on a basis of an average value of luminance values of pixels forming said outside light image.

4. The image processing device according to claim 1, wherein said adjusting means adjusts the parameter of said image pickup means on a basis of a luminance value of a maximum number of pixels among luminance values of pixels forming said outside light image.

5. The image processing device according to claim 1, wherein said adjusting means adjusts the parameter of said image pickup means on a basis of a luminance value of a pixel when a luminance integration count obtained by performing integration starting with a pixel having a low luminance value becomes a predetermined value among luminance values of pixels forming said outside light image.

6. The image processing device according to claim 1, wherein said adjusting means adjusts at least one of a gain of said image pickup means, receiving sensitivity, and light reception time as the parameter of said image pickup means.

7. The image processing device according to claim 1, wherein said first irradiating means and said second irradiating means apply infrared rays of respective different wavelengths.

8. The image processing device according to claim 7, wherein one of said first irradiating means and said second irradiating means applies light of a wavelength equal to or more than 930 nm, and the other applies light of less than 930 nm.

9. An image processing method of an image processing device for detecting a skin region representing a skin of a subject from a pickup image obtained by imaging said subject, the image processing device including first irradiating means, second irradiating means, image pickup means, adjusting means, and skin detecting means, the image processing method comprising:
    said first irradiating means irradiating said subject with light of a first wavelength;
    said second irradiating means irradiating said subject with light of a second wavelength different from said first wavelength;

said image pickup means imaging said subject;

said adjusting means adjusting a parameter of said image pickup means within a range in which a skin detectable condition for detecting said skin region is satisfied on a basis of an outside light image obtained by imaging said subject by said image pickup means in a state of said subject not being irradiated with light of said first wavelength or light of said second wavelength; and said skin detecting means detecting said skin region on a basis of a first pickup image obtained by imaging said subject when said subject is irradiated with light of said first wavelength by said image pickup means having the parameter adjusted by said adjusting means and a second pickup image obtained by imaging said subject when said subject is irradiated with light of said second wavelength by said image pickup means having the parameter adjusted by said adjusting means, said adjusting means adjusting the parameter of said image pickup means within a range in which said skin detectable condition that a luminance value of a pixel forming said outside light image be equal to or lower than half of a maximum luminance value that can be obtained by imaging of said image pickup means is satisfied.

10. A non-transitory computer readable medium including a program for making a computer function as:

adjusting means for adjusting a parameter of image pickup means within a range in which a skin detectable condition for detecting a skin region representing a skin of a subject is satisfied on a basis of an outside light image obtained by imaging said subject by said image pickup means in a state of said subject not being irradiated with light of a first wavelength or light of a second wavelength different from said first wavelength; and skin detecting means for detecting said skin region on a basis of a first pickup image obtained by imaging said subject when said subject is irradiated with light of said first wavelength by said image pickup means having the parameter adjusted by said adjusting means and a second pickup image obtained by imaging said subject when said subject is irradiated with light of said second wavelength by said image pickup means having the parameter adjusted by said adjusting means wherein said adjusting means adjusts the parameter of said image pickup means within a range in which said skin detectable condition that a luminance value of a pixel forming said outside light image be equal to or lower than half of a maximum luminance value that can be obtained by imaging of said image pickup means is satisfied.

11. An electronic device including an image processing device for detecting a skin region representing a skin of a subject from a pickup image obtained by imaging said subject, wherein said image processing device includes:

first irradiating means for irradiating said subject with light of a first wavelength;

second irradiating means for irradiating said subject with light of a second wavelength different from said first wavelength;

image pickup means for imaging said subject;

adjusting means for adjusting a parameter of said image pickup means within a range in which a skin detectable condition for detecting said skin region is satisfied on a basis of an outside light image obtained by imaging said subject by said image pickup means in a state of said subject not being irradiated with light of said first wavelength or light of said second wavelength; and skin detecting means for detecting said skin region on a basis of a first pickup image obtained by imaging said subject when said subject is irradiated with light of said first wavelength by said image pickup means having the parameter adjusted by said adjusting means and a second pickup image obtained by imaging said subject when said subject is irradiated with light of said second wavelength by said image pickup means having the parameter adjusted by said adjusting means, wherein said adjusting means adjusts the parameter of said image pickup means within a range in which said skin detectable condition that a luminance value of a pixel forming said outside light image be equal to or lower than half of a maximum luminance value that can be obtained by imaging of said image pickup means is satisfied.

12. An image processing device for detecting a skin region representing a skin of a subject from a pickup image obtained by imaging said subject, the image processing device comprising:

a first irradiating section configured to irradiate said subject with light of a first wavelength;

a second irradiating section configured to irradiate said subject with light of a second wavelength different from said first wavelength;

an image pickup section configured to image said subject;

an adjusting section configured to adjust a parameter of said image pickup section within a range in which a skin detectable condition for detecting said skin region is satisfied on a basis of an outside light image obtained by imaging said subject by said image pickup section in a state of said subject not being irradiated with light of said first wavelength or light of said second wavelength; and a skin detecting section configured to detect said skin region on a basis of a first pickup image obtained by imaging said subject when said subject is irradiated with light of said first wavelength by said image pickup section having the parameter adjusted by said adjusting section and a second pickup image obtained by imaging said subject when said subject is irradiated with light of said second wavelength by said image pickup section having the parameter adjusted by said adjusting section, wherein said adjusting section adjusts the parameter of said image pickup means within a range in which said skin detectable condition that a luminance value of a pixel forming said outside light image be equal to or lower than half of a maximum luminance value that can be obtained by imaging of said image pickup means is satisfied.

13. An image processing device for detecting a skin region representing a skin of a subject from a pickup image obtained by imaging said subject, the image processing device comprising:

first irradiating means for irradiating said subject with light of a first wavelength;

second irradiating means for irradiating said subject with light of a second wavelength different from said first wavelength;

image pickup means for imaging said subject;

adjusting means for adjusting a parameter of said image pickup means within a range in which a skin detectable condition for detecting said skin region is satisfied on a basis of an outside light image obtained by imaging said subject by said image pickup means in a state of said subject not being irradiated with light of said first wavelength or light of said second wavelength; and skin detecting means for detecting said skin region on a basis of a first pickup image obtained by imaging said subject when said subject is irradiated with light of said first wavelength by said image pickup means having the parameter adjusted by said adjusting means and a second pickup image obtained by imaging said subject when said subject is irradiated with light of said second wavelength by said image pickup means having the parameter adjusted by said adjusting means, wherein said adjusting means adjusts the parameter of said image pickup means on a basis of a luminance value of a pixel when a luminance integration count obtained by performing integration starting with a pixel having a low luminance value becomes a predetermined value among luminance values of pixels forming said outside light image.

* * * * *